United States Patent [19]

Lalezari et al.

[11] Patent Number: 5,385,731
[45] Date of Patent: Jan. 31, 1995

[54] METHOD OF TREATING HYPERLIPIDEMIA WITH GRANULOCYTE COLONY STIMULATING FACTOR

[75] Inventors: Parviz Lalezari, Scarsdale; Manouchehr Khorshidi, Great Neck, both of N.Y.

[73] Assignee: Montefiore Medical Center, Bronx, N.Y.

[21] Appl. No.: 795,929

[22] Filed: Nov. 14, 1991

[51] Int. Cl.⁶ .............................................. A61K 37/02
[52] U.S. Cl. ...................................... 424/85.1; 514/12
[58] Field of Search .......................... 424/85.1; 514/12

[56] References Cited

U.S. PATENT DOCUMENTS 5,019,381  5/1991  Garnick ................................. 514/2

OTHER PUBLICATIONS

Rosenfeld, A. J. Path, vol. 140, No. 2, pp. 291–300 (Feb. 1992).
Clinton et al., A. J. Bath, vol. No. 2, pp. 301–316.

*Primary Examiner*—Howard E. Schain
*Assistant Examiner*—Lynn Touzeau
*Attorney, Agent, or Firm*—Hedman, Gibson & Costigan

[57] ABSTRACT

A novel method for the treatment of hyperlipidemia/-high serum cholesterol is disclosed which is based on the parenteral administration of granulocyte colony stimulating factor.

11 Claims, No Drawings

METHOD OF TREATING HYPERLIPIDEMIA WITH GRANULOCYTE COLONY STIMULATING FACTOR

BACKGROUND OF THE INVENTION

The present invention is concerned with the administration of granulocyte colony stimulating factor (GCSF) to a host for the purpose of reducing serum lipid levels including the level of serum cholesterol.

Many efforts have been made to reduce plasma lipids in connection with efforts to reduce the risk of coronary heart disease. Chemical agents that have been used for this purpose include niacin, D-thyroxine, probucol and cholestyramine.

These agents have had relative success but have had many unpleasant side effects which have restricted their use. It is believed that GCSF does not have the undesirable side effects which limit the use of the prior art materials while it will exert a profound lowering effect on serum cholesterol levels.

Accordingly, it is a primary object of this invention to provide a novel method for treating hyperlipidemia.

It is also an object of this invention to provide a novel method for treating high serum cholesterol levels.

SUMMARY OF THE INVENTION

The invention is based on the administration to a mammal of an amount of GCSF which is effective to treat hyperlipidemia or high serum cholesterol. The GCSF is administered parenterally.

DETAILED DESCRIPTION OF THE INVENTION

The product known as GCSF is commercially available and may be prepared according to methods described in the literature. See *Derwent Biotechnology Abstracts* 90-07568 and 90-10013; EP-355811, 90-060563/09 Feb. 29, 1990; JP-210376, Aug. 24, 1990, all of which are incorporated by reference. The preferred GCSF is derived from a human cell line.

The usual dose may be 0.5-50 µg per kilogram of body weight daily given 1 to 7 times a week or preferably 2-10 µg per kilogram of body weight daily given every other day. The dose will depend upon the lipid or cholesterol level in a particular patients serum as well as the neutrophil response (white blood cell) of the individual patient. It is advisable to monitor the patients response to the drug through periodic blood tests to verify the response and provide a basis on which to adjust the dose.

The drug is preferably administered parenterally i.e. subcutaneously or intramuscular although if proper precautions are observed it may be administered intravenously. In addition, the drug may be administered by contacting the mucosal membrane such as the nasal membrane or by transdermal patches.

The drug may be given to mammals including humans who are candidates for reduction of total serum lipids or serum cholesterol.

I claim:

1. A method for the treatment of hyperlipidemia in mammals which comprises administering to a mammal with hyperlipidemia an amount of granulocyte colony stimulating factor which is sufficient to treat hyperlipidemia.

2. A method as defined in claim 1, wherein 0.5-50 µg of granulocyte colony stimulating factor per kilogram of body weight is administered parenterally 1 to 7 times a week.

3. A method for lowering serum cholesterol in mammals which comprises administering to a mammal with high serum cholesterol an amount of granulocyte colony stimulating factor which is sufficient to treat high serum cholesterol.

4. A method as defined in claim 3, wherein 0.5-50 µg per kilogram of body weight is administered parenterally 1 to 7 times a week.

5. A method as defined in claim 2 wherein 2-10 µg per kilogram of body weight are administered to a human every other day.

6. A method as defined in claim 1 wherein the mammal is a human.

7. A method as defined in claim 2 wherein the mammal is a human.

8. A method as defined in claim 3 wherein the mammal is a human.

9. A method as defined in claim 4 wherein the mammal is a human.

10. A method as defined in claim 5 wherein the mammal is a human.

11. A method of treating high serum cholesterol in a mammalian host afflicted with high serum cholesterol said method consisting essentially of administering from 0.5-50 µg of granulocyte colony stimulating factor to said host, parenterally 1 to 7 times a week.

* * * * *